(12) United States Patent
Lee

(10) Patent No.: US 12,154,369 B2
(45) Date of Patent: Nov. 26, 2024

(54) DISPLAY DEVICE AND DRIVING METHOD THEREOF

(71) Applicant: SAMSUNG DISPLAY CO., LTD., Yongin-si (KR)

(72) Inventor: Soon Gyu Lee, Yongin-si (KR)

(73) Assignee: SAMSUNG DISPLAY CO., LTD., Yongin-si (KR)

( * ) Notice: Subject to any disclaimer, the term of this patent is extended or adjusted under 35 U.S.C. 154(b) by 97 days.

(21) Appl. No.: 17/450,844

(22) Filed: Oct. 14, 2021

(65) Prior Publication Data

US 2022/0198174 A1 Jun. 23, 2022

(30) Foreign Application Priority Data

Dec. 17, 2020 (KR) .................. 10-2020-0177890

(51) Int. Cl.
*G06V 40/13* (2022.01)
*A61B 5/00* (2006.01)
(Continued)

(52) U.S. Cl.
CPC .......... *G06V 40/1318* (2022.01); *A61B 5/442* (2013.01); *A61B 5/443* (2013.01);
(Continued)

(58) Field of Classification Search
CPC .......... G06V 40/1318; G06V 40/1306; G06V 40/12–1394; A61B 5/442; A61B 5/443;
(Continued)

(56) References Cited

U.S. PATENT DOCUMENTS 8,238,623 B2 * 8/2012 Stephan ................ G06T 7/0012
382/160
10,993,657 B1 * 5/2021 Miller .................... A61B 5/681
(Continued)

FOREIGN PATENT DOCUMENTS

JP 4739746 8/2011
KR 10-2015-0117074 10/2015
(Continued)

OTHER PUBLICATIONS

Extended European Search Report dated May 13, 2022 in corresponding European Patent Application No. 21215243.3 (12 pages).
(Continued)

*Primary Examiner* — Roberto W Flores
(74) *Attorney, Agent, or Firm* — F. Chau & Associates, LLC

(57) ABSTRACT

A display device includes a touch sensor, a fingerprint sensor, and a sensor driver. The touch sensor generates a touch sensing signal in response to touch of an object on a display panel. The fingerprint sensor detects the object in a first mode to generate a first sensing signal and detects the object in a second mode to generate a second sensing signal. The sensor driver calculates a touch position and a moisture level of the object based on the touch sensing signal, generates fingerprint information based on the first sensing signal, and corrects the moisture level based on the second sensing signal.

23 Claims, 18 Drawing Sheets

(51) Int. Cl.
*G09G 3/3233* (2016.01)
*G09G 3/3266* (2016.01)

(52) U.S. Cl.
CPC ....... *G06V 40/1306* (2022.01); *G09G 3/3233* (2013.01); *G09G 3/3266* (2013.01)

(58) Field of Classification Search
CPC .. A61B 5/4875; G09G 3/3233; G09G 3/3266; G06F 3/041–047
See application file for complete search history.

(56) References Cited

U.S. PATENT DOCUMENTS

| | | |
|---|---|---|
| 2007/0276206 A1 | 11/2007 | Takeuchi et al. |
| 2008/0194928 A1 | 8/2008 | Bandic et al. |
| 2012/0016798 A1* | 1/2012 | Carper ............... G06V 40/1365 340/5.83 |
| 2016/0042219 A1* | 2/2016 | Bae ....................... G06V 40/70 382/124 |
| 2016/0274726 A1* | 9/2016 | Chung .................... G06F 3/014 |
| 2018/0225495 A1* | 8/2018 | Jonsson .............. G06V 40/1329 |
| 2018/0276439 A1 | 9/2018 | Strohmann et al. |
| 2018/0276440 A1* | 9/2018 | Strohmann ........ G06V 40/1359 |
| 2018/0285619 A1* | 10/2018 | Kim ....................... G06V 40/13 |
| 2018/0353109 A1* | 12/2018 | Li ........................ A61B 5/4875 |
| 2019/0125249 A1 | 5/2019 | Rattner et al. |
| 2019/0159717 A1* | 5/2019 | Park ........................ G06F 3/044 |
| 2020/0241665 A1* | 7/2020 | Fu ....................... G06F 3/04166 |
| 2020/0345294 A1 | 11/2020 | Varghese et al. |

FOREIGN PATENT DOCUMENTS

| | | |
|---|---|---|
| KR | 10-2016-0112559 | 9/2016 |
| KR | 10-2175348 | 11/2020 |

OTHER PUBLICATIONS

Olsen, et al., "Fingerprint skin moisture impact on biometric performance", 3rd International Workshop on Biometrics and Forensics (IWBF 2015), IEEE, Mar. 3, 2015, pp. 1-6, XP032779934.

* cited by examiner

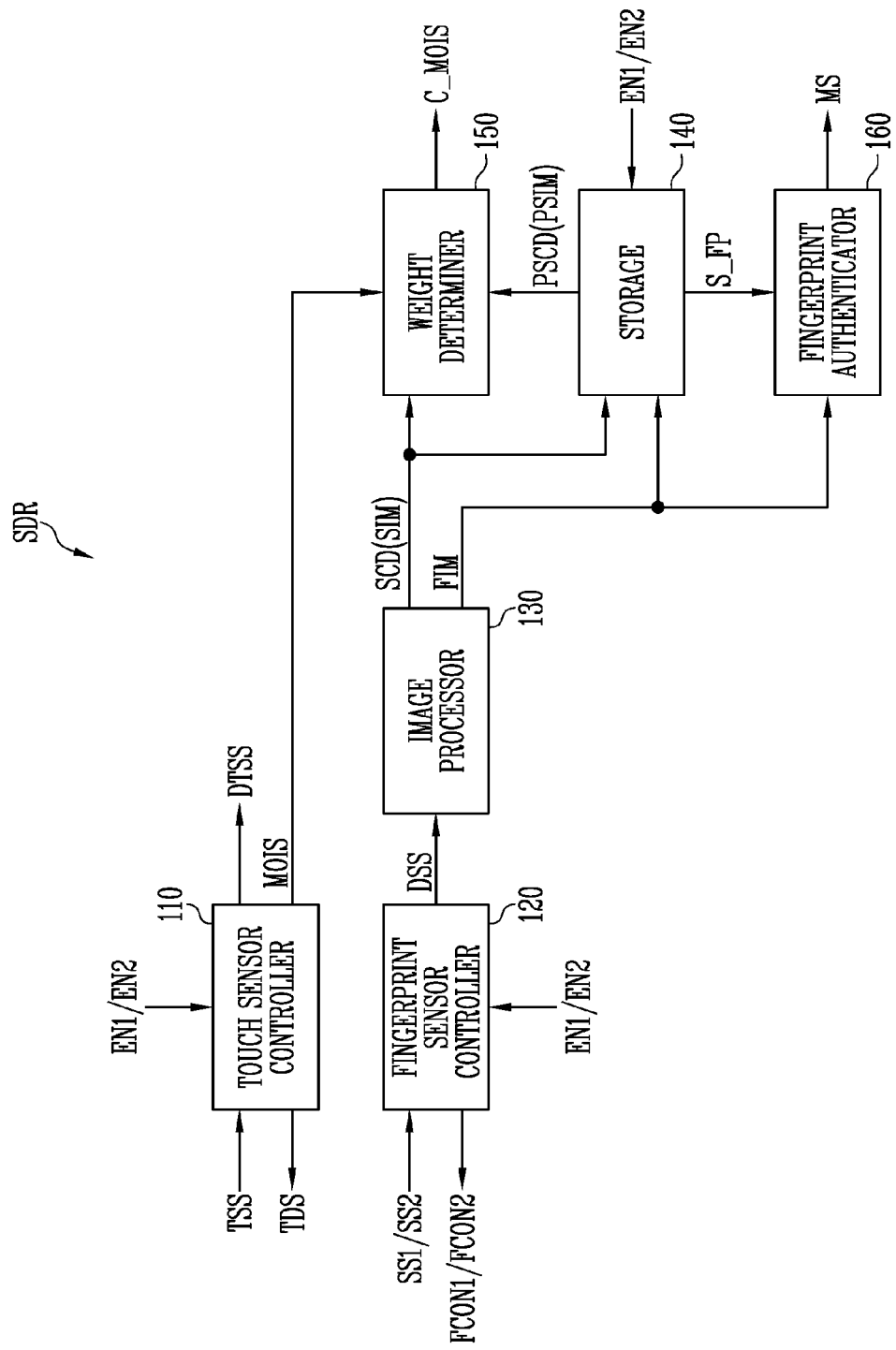

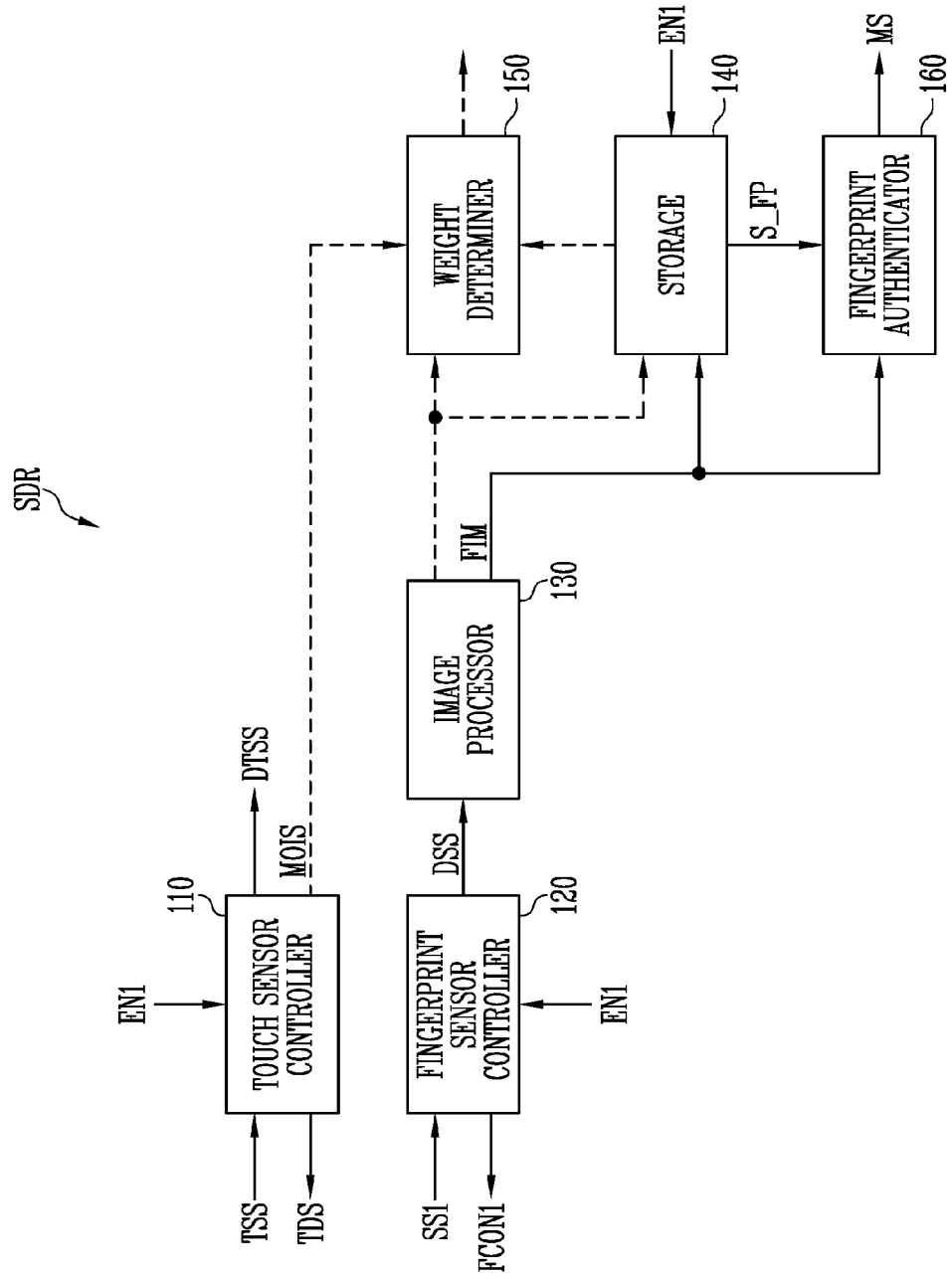

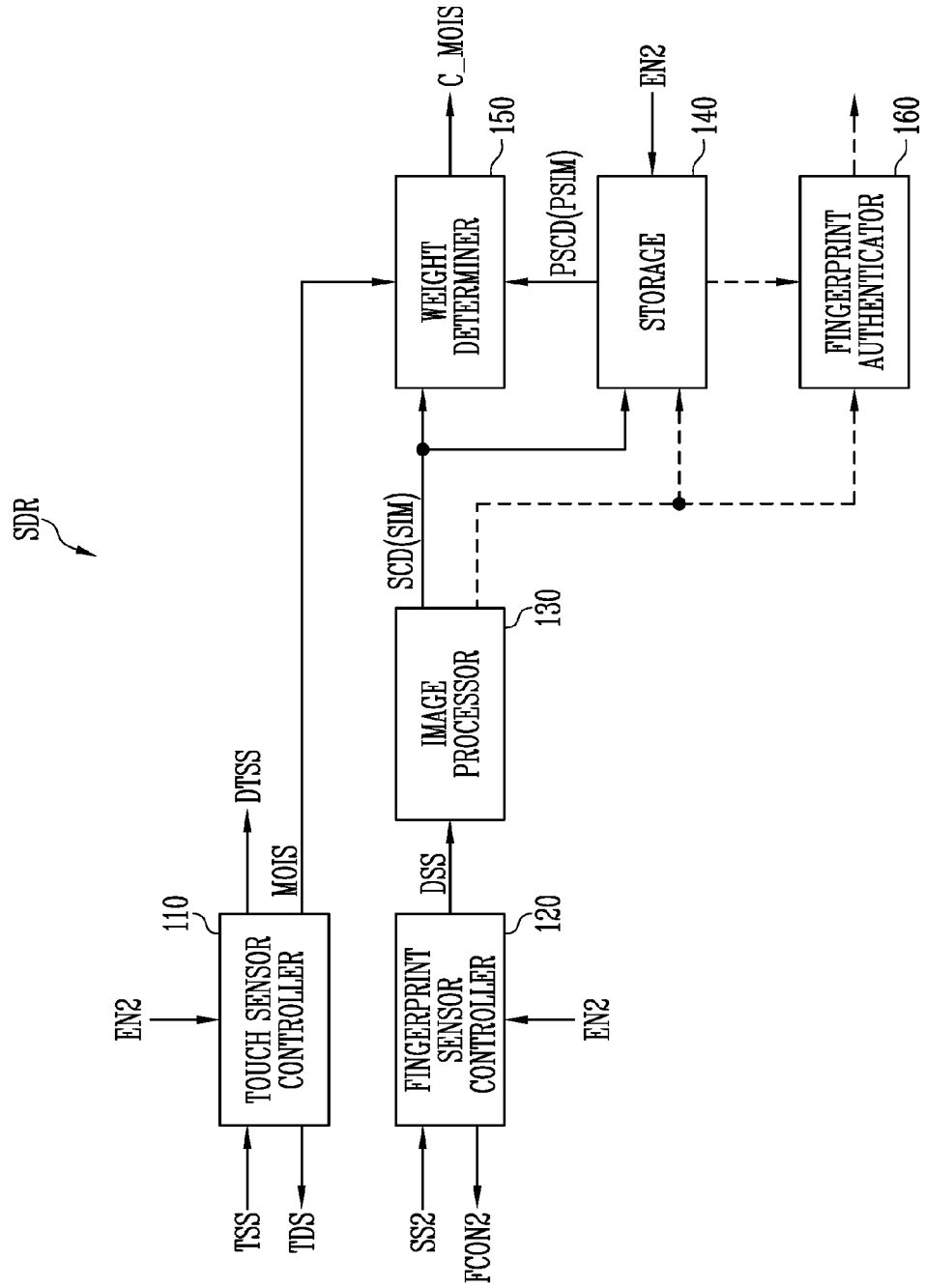

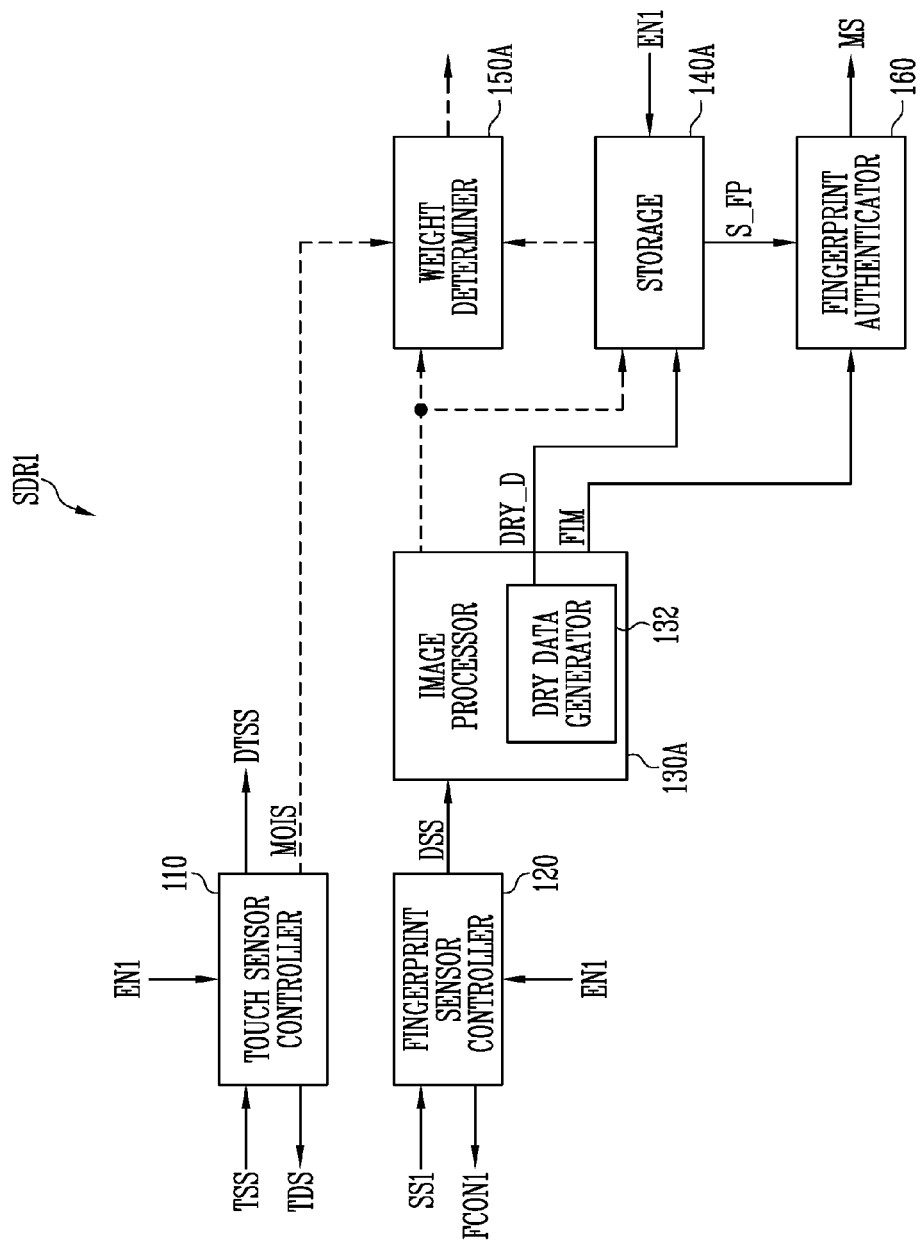

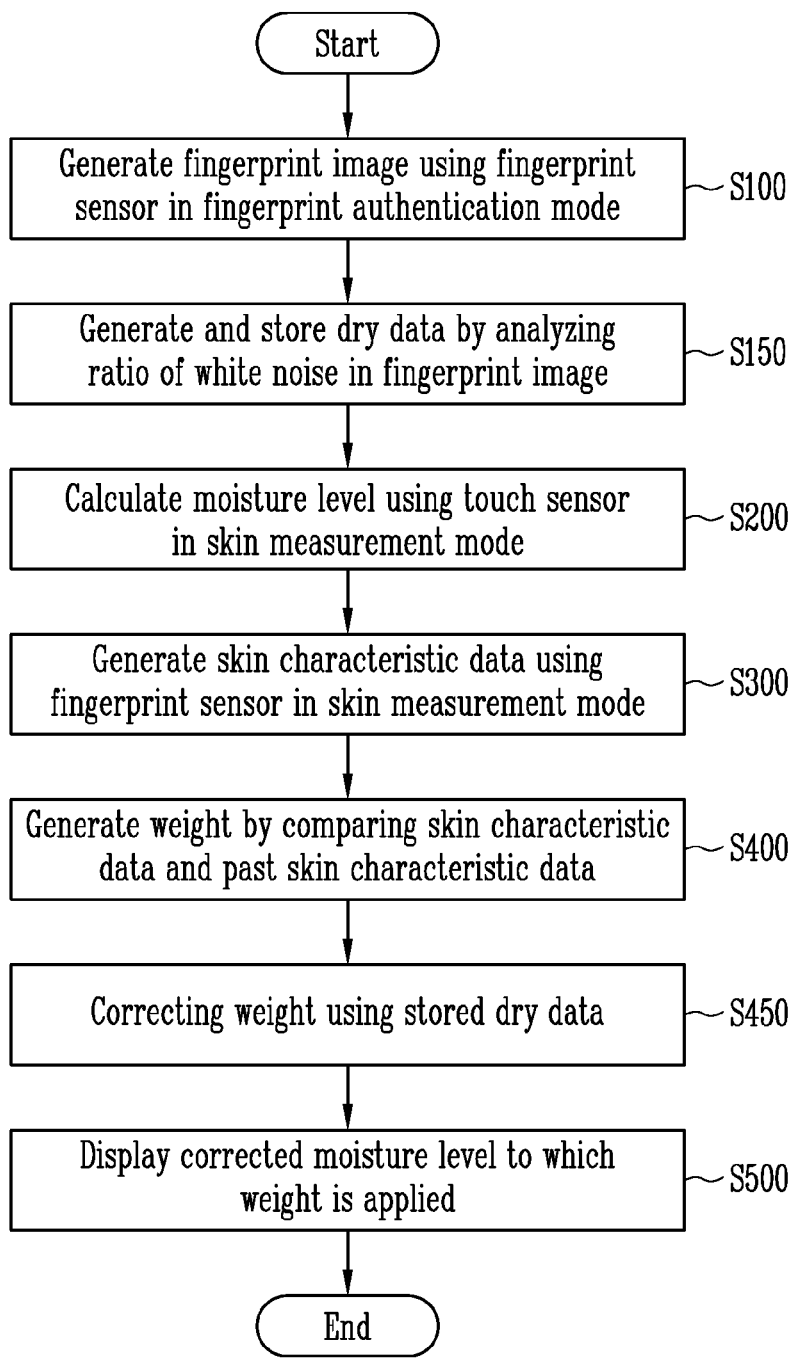

DISPLAY DEVICE AND DRIVING METHOD THEREOF

CROSS-REFERENCE TO RELATED APPLICATION

This application claims priority to and the benefit of Korean Patent Application No. 10-2020-0177890, filed in the Korean Intellectual Property Office on Dec. 17, 2020, the entire contents of which are incorporated by reference herein.

BACKGROUND OF THE INVENTION

1. Field of the Invention

One or more embodiments described herein relate to a display device, and method of driving a display device.

2. Description of the Related Art

A variety of multimedia electronic devices have been developed. Examples include televisions, smart phones, tablet computers, computers, navigation systems, game devices, and wearable devices. Many of these have touch panels that allow users to input information and instructions. In addition, some have sensors for capturing biometric information.

SUMMARY OF THE INVENTION

One or more embodiments described herein provide a display device that operates based on the moisture level of skin or other touch object.

One or more embodiments may obtain a skin moisture level measurement based on data sensed by a fingerprint sensor.

One or more embodiments may correct the skin level moisture measurement to control operation of the display device.

One or more embodiments provide a method of driving a display device, which, for example, may correspond to the aforementioned display device.

In accordance with one or more embodiments, display device includes a display panel including pixels, a touch sensor on a surface of the display panel and configured to generate a touch sensing signal in response to touch of an object; a fingerprint sensor spaced apart from the touch sensor and configured to detect the object in a first mode to generate a first sensing signal and to detect the object in a second mode to generate a second sensing signal; and a sensor driver configured to calculate a touch position and a moisture level of the object based on the touch sensing signal, generate fingerprint information based on the first sensing signal, and correct the moisture level based on the second sensing signal.

In accordance with one or more embodiments, a method of driving a display device includes calculating a moisture level using a touch sensing signal generated by a touch sensor in a skin measurement mode, generating skin characteristic data using a skin sensing signal generated by a fingerprint sensor in the skin measurement mode, generating a weight based on a comparison of the skin characteristic data with accumulated past skin characteristic data, correcting the moisture level based on the weight, and displaying an image indicating the corrected moisture level.

In accordance with one or more embodiments, a non-transitory computer-readable medium storing instructions which, when executed by one or more processors, cause the one or more processors to calculate a moisture level using a touch sensing signal generated by a touch sensor in a skin measurement mode, generate skin characteristic data using a skin sensing signal generated by a fingerprint sensor in the skin measurement mode, generate a weight based on a comparison of the skin characteristic data with accumulated past skin characteristic data, correct the moisture level based on the weight; and display an image indicating the corrected moisture level.

BRIEF DESCRIPTION OF THE DRAWINGS

FIG. 4A illustrates an embodiment of a sensor driver,
and FIG. 4B and FIG. 4C illustrate operations of the sensor driver according to one or more embodiments.
FIGS. 11B and 11C illustrate operations of the sensor driver according to one or more embodiments.
FIG. 14 illustrates an embodiment of a method of driving a display device.

DETAILED DESCRIPTION OF THE EMBODIMENTS

Figure 1A:
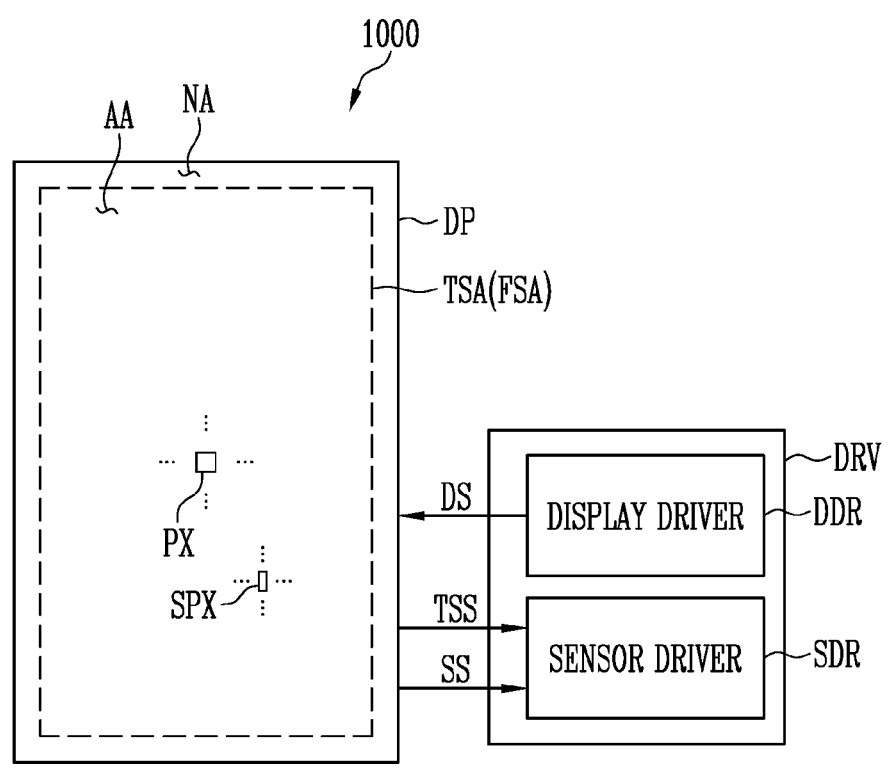
FIGS. 1A and 1B illustrate embodiments of a display device.

Hereinafter, an embodiment of the present invention will be described in detail with reference to the accompanying drawings. Like reference numerals are used for like constituent elements on the drawings, and duplicate descriptions for the like constituent elements are omitted.

Figure 1B:
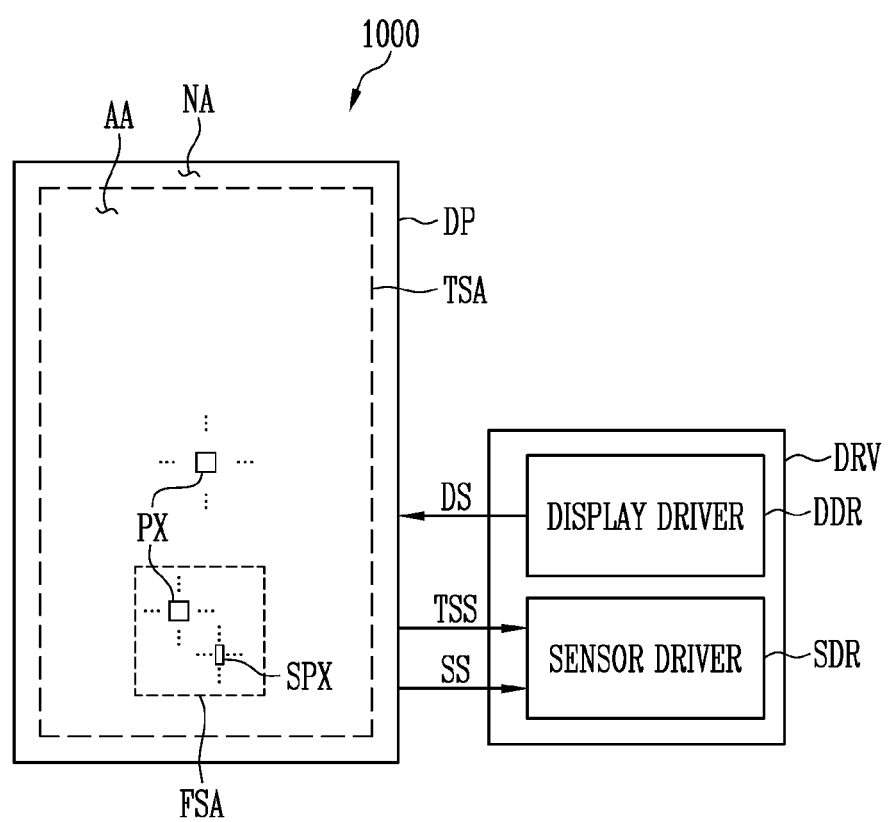
Figure 2:
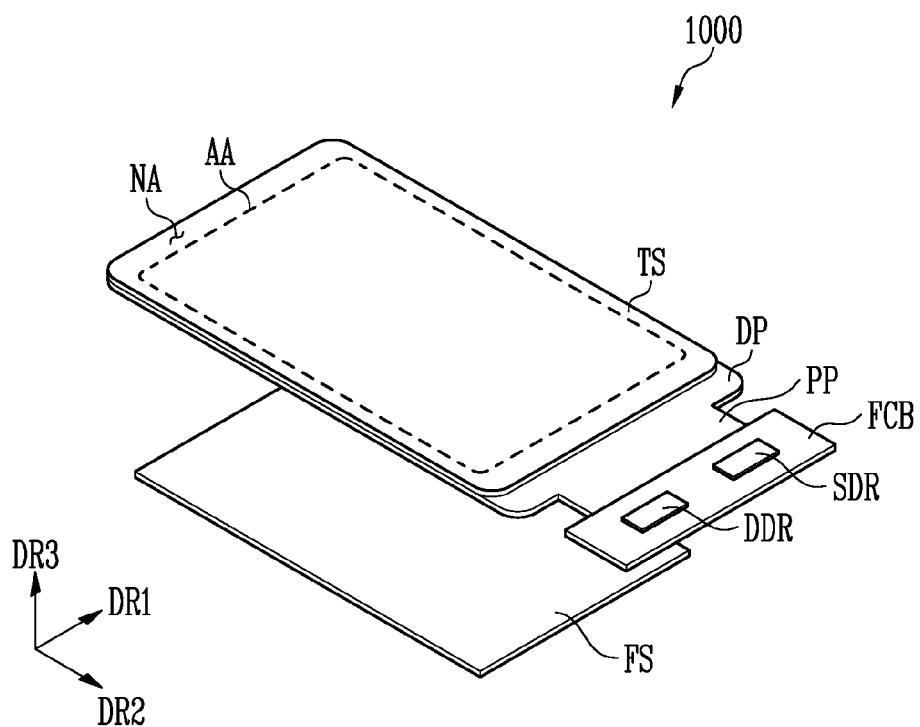
FIG. 2 illustrates an example perspective view of a display device.

FIGS. 1A and 1B illustrate embodiments of a display device 1000, and FIG. 2 illustrates an exploded perspective view of an embodiment of the display device 1000 of FIG. 1A.

Referring to FIGS. 1A and 1B, the display device 1000 may include a display panel DP, a touch sensor TS, a fingerprint sensor FS, and a driver DRV. The driver DRV may include a display driver DDR and a sensor driver SDR. In an embodiment, the display device 1000 may further include a printed circuit board FCB on which at least a portion of the driver DRV is mounted.

All or a portion of the display device 1000 may be flexible. In one embodiment, the display device 1000 may be implemented as a self-light emitting display device including a plurality of self-light emitting elements. For example, the display device 1000 may be an organic light emitting diode display including organic light emitting elements, a display device including inorganic light emitting elements, or a display device including light emitting elements made of a combination of inorganic and organic materials. However, display device 1000 may be implemented as a liquid crystal display, a plasma display device, a quantum dot display device, or another type of display in another embodiment. Light emitting elements in the display panel DP of the quantum dot display device may include a quantum dot and/or a quantum rod.

The display device 1000 may be a flat panel display device, a flexible display device, a curved display device, a foldable display device, or a bendable display device. In addition, the display device may be applied to a transparent display device, a head-mounted display device, a wearable display device, and the like.

As shown in FIG. 2, a display surface on which an image is displayed may be parallel to a plane extending in a first direction axis DR1 and a second direction axis DR2. A normal direction of the display surface (e.g., a thickness direction) of the display device 1000 may correspond to a third direction axis DR3.

The display panel DP may include a display area AA and a non-display area NA. The display area AA includes a plurality of pixels PX (or in one embodiment synonymously referred to as subpixels) in an active area. Each of the pixels PX may include at least one light emitting element. The display device 1000 displays an image in the display area AA by driving the pixels PX in response to image data input from an external source.

The non-display area NA is around the display area AA and may be referred to as a non-active area. For example, the non-display area NA includes a pad area PP, and may further include a wire area and various dummy areas. The printed circuit board FCB may be attached to the pad area PP.

In the embodiment, the display area AA may include a touch sensing area TSA implemented by the touch sensor TS. For example, the touch sensor TS may correspond to the display area AA of the display panel DP, and in one embodiment the touch sensing area TSA may be entirely or partially formed on the display area AA as shown in FIGS. 1A and 1B.

As shown, for example, in FIG. 2, the touch sensor TS may be disposed on the display panel DP to correspond to the touch sensing area TSA. The touch sensor TS may include sensing electrodes arranged to correspond to the touch sensing area TSA. In the embodiment, the touch sensor TS may be a capacitive touch sensor. For example, some of the sensing electrodes may receive a touch driving signal, and some other of the sensing electrodes may output a change in capacitance between the sensing electrodes as a touch sensing signal TSS. When a body part of a user is disposed on capacitance-coupled sensing electrodes, capacitance between the sensing electrodes may be changed.

The display area AA may include a fingerprint sensing area FSA implemented by the fingerprint sensor FS. For example, the fingerprint sensor FS may include one or more sensor pixels SPX. The fingerprint sensing area FSA may overlap the sensor pixels SPX. The fingerprint sensing area FSA may overlap at least a portion of the touch sensing area TSA. For example, as shown in FIG. 1A, the fingerprint sensing area FSA may be formed to be substantially the same as the display area AA and/or the touch sensing area TSA. In the embodiment of FIG. 1B, a portion of the display area AA may be set as the fingerprint sensing area FSA. In an embodiment, the touch sensing area TSA and the fingerprint sensing area FSA may be formed in at least a portion of the non-display area NA of the display panel DP.

In one embodiment, the sensor pixels SPX may be configured as optical sensors for sensing light. The sensor pixels SPX may output an electrical signal (for example, a voltage signal) based on sensing a light reflected from skin on a finger or other body part of a user. The source of the reflected light may be light emitted from a light source (e.g., a backlight, light from one or more pixels PX, etc.) in the display device 1000. The electrical signal of each sensor pixel SPX may configure one point (that is, a point of contrast or pixel, which, for example, may be a minimum unit configuring a fingerprint image) within the fingerprint image. The reflected light may have different characteristics (for example, frequency, wavelength, size, etc.) depending on whether the light incident on respective sensor pixels SPX is reflected by a valley of the fingerprint (or skin pattern such as a palm or skin feature) or by a ridge thereof. Accordingly, the sensor pixels SPXL may output sensing signals SS having different electrical characteristics corresponding to the light characteristics of the reflected light.

When the sensor pixels SPX are disposed in the fingerprint sensing area FSA, the sensor pixels SPX may overlap the pixels PX or may be disposed around the pixels PX. For example, some or all of the sensor pixels SPX may overlap the pixels PX or may be disposed between the pixels PX. In various embodiments, the sensor pixels SPX and the pixels PX may have substantially the same or different sizes. The relative size and arrangement between sensor pixels SPX and the pixels PX may vary among embodiments.

In one embodiment, the sensor pixels SPX may configure an ultrasonic wave sensor for sensing ultrasonic waves. For example, the sensor pixels SPX may emit an ultrasonic wave signal and may sense an ultrasonic wave reflected by a finger and output corresponding electrical signals (or the sensing signal SS). In the embodiment, the sensor pixels SPX may configure a capacitive sensor of which capacitance is changed according to a shape of a fingerprint.

In the embodiment of FIG. 2, the fingerprint sensor FS including sensor pixels SPX may be disposed on a rear surface (for example, a back surface) opposite to a surface (for example, front surface) on which an image is displayed, among respective surfaces of the display panel DP. However, the present invention is not limited thereto. For example, the sensor pixels SPX (that is, the fingerprint sensor FS) may be between the touch sensor TS and the display panel DP or may be between the sensing electrodes of the touch sensor.

In one embodiment, the display driver DDR and the sensor driver SDR may be on the printed circuit board FCB. However, constituent elements of the display driver DDR and the sensor driver SDR may be directly disposed on the display panel (DP).

The display driver DDR may drive the display panel DP. For example, the display driver DDR may output a data signal DS corresponding to image data to the display panel DP.

The sensor driver SDR may drive the touch sensor TS and the fingerprint sensor FS. In one embodiment, the sensor driver SDR may provide a touch driving signal for driving the touch sensor TS (sensing electrodes). The sensor driver SDR may detect a change in capacitance of the touch sensing signal TSS received from the touch sensor TS and then calculate coordinates of a touch position. In addition, the sensor driver SDR may detect a change in capacitance of the touch sensing signal TSS and then calculate the skin condition of a user. The skin condition may be, for example, a skin moisture level or skin hydration level.

In one embodiment, the sensor driver SDR may output a driving signal control signal for the sensor pixel SPX of the fingerprint sensor FS, and may receive sensing signal SS received from the sensor pixels SPX. For example, the sensing signal SSsupplied from the fingerprint sensor FS in a first mode is a first sensing signal, and the sensing signal SS supplied from the fingerprint sensor FS in a second mode is a second sensing signal. These sensing signals may be distinguished from each other. The first mode may be a fingerprint authentication mode for authenticating a fingerprint, and the second mode may be a skin measurement mode for detecting skin characteristics (e.g., moisture level) of a user.

The sensor driver SDR may detect or recognize a fingerprint based on the sensing signal SS received in the first mode. For example, the sensor driver SDR may convert the sensing signal SS to a fingerprint image (or fingerprint image data, fingerprint information) and may perform fingerprint authentication based on the fingerprint image. The sensor pixels SPX and sensor driver SDR may configure a fingerprint authentication device. The sensor driver SDR may calculate skin characteristics (skin characteristic data) based on the sensing signal SS received in the second mode, and may correct the calculated moisture level (skin moisture level) based on the touch sensing signal TSS.

Figure 3:
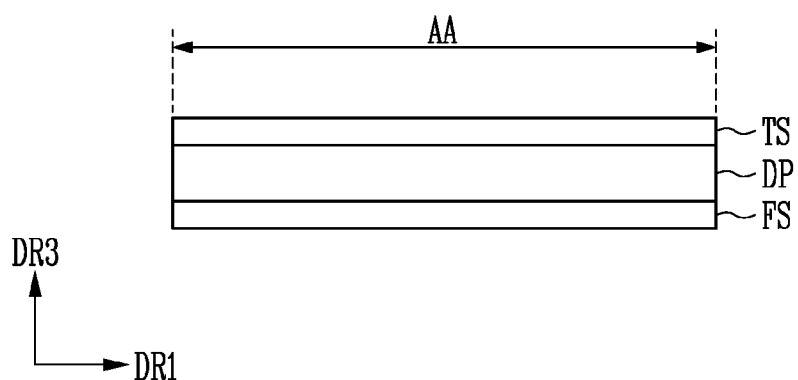
FIG. 3 illustrates an example of a display area.

FIG. 3 illustrates a cross-sectional view of a display area of the display device 1000 of FIG. 1A according to an embodiment. In particular, FIG. 3 shows a cross-section of the display area AA of the display device 1000 defined by the first direction axis DR1 and the third direction axis DR3. Constituent elements of the display device 1000 are illustrated to explain an example relationship in which they are stacked.

Referring to FIG. 3, the display device 1000 may include the display panel DP, the touch sensor TS, and the fingerprint sensor FS. Constituent elements of at least some of the display panel DP, the touch sensor TS, and the fingerprint sensor FS may be formed by a continuous process, or the constituent elements of at least some thereof may be bonded to each other through an adhesive member.

In one embodiment, the touch sensor TS may be formed with the display panel DP through a continuous process and may be directly disposed on the display panel DP. In one embodiment, disposing a constituent element "B" directly disposed on a constituent element "A" may mean that a separate adhesive layer/adhesive member is not disposed between the constituent elements "A" and "B". In one embodiment, constituent element "B" may be formed through a continuous process on a uppermost layer (base surface) provided by the constituent element "A," after the constituent element "A" is formed.

In one embodiment, the touch sensor TS may be disposed on the display panel DP in a "panel" type. For example, the touch sensor TS may include a unique base layer (or substrate), and the touch sensor TS and the display panel DP may be coupled to each other by a predetermined adhesive member. For example, the adhesive member may be a transparent adhesive member such as a pressure sensitive adhesive film (PSA), an optically clear adhesive film (OCA), or an optically clear adhesive resin (OCR).

In one embodiment, the fingerprint sensor FS may be disposed on a back of the display panel DP. The fingerprint sensor FS and the display panel DP may be formed through a continuous process or may be coupled to each other by an adhesive member. In one embodiment, the fingerprint sensor FS may be between the touch sensor TS and the display panel DP. In one embodiment, at least some of the sensing electrodes of the touch sensor TS and the at least a portion of the sensor pixel SPX of the fingerprint sensor FS may be spaced apart from each other on the same layer. In one embodiment, at least a portion of the touch sensor TS and the fingerprint sensor FS may be inserted into the display panel DP or may be coupled to the display panel DP.

FIG. 4A illustrates a block diagram of an embodiment of a sensor driver in or coupled to the display device 1000 of FIGS. 1A and 1B.

Referring to FIGS. 1A, 1B, 2, and 4A, the sensor driver SDR may include a touch sensor controller 110, a fingerprint sensor controller 120, an image processor 130, a storage 140, and a weight determiner (or calculator) 150. The sensor driver SDR may further include a fingerprint authenticator 160.

The sensor driver SDR may be driven in response to a first enable signal EN1 activated in the first mode or a second enable signal EN2 activated in the second mode. The first and second enable signals EN1 and EN2 may be applied through separate signal lines or may be determined according to high/low levels of a signal through one signal line. For example, a first (e.g., logic high) level of a predetermined signal may be activated in the first mode as the first enable signal EN1, and a second (e.g., logic low) level thereof may be activated in the second mode as the second enable signal EN2. However, the opposite may be the case in another embodiment.

The touch sensor controller 110 may control driving of the touch sensor TS and may calculate a moisture level MOIS based on the touch sensing signal TSS. The touch sensor controller 110 may supply a touch driving signal TDS to the touch sensor. The touch sensor TS may output a change in capacitance according to a user touch as the touch sensing signal TSS.

The touch sensor controller 110 may calculate a touch position of an object (e.g., a finger or the like) and the moisture level MOIS of the object based on the touch sensing signal TSS. In the embodiment, the touch sensor controller 110 may include an analog-digital converter that converts a touch sensing signal TSS to a digital value. In one embodiment, touch sensor controller 110 may convert the touch sensing signal TSS to a digital touch sensing signal DTSS including touch position coordinate information or may use the touch sensing signal TSS to calculate a digital format of moisture level MOIS.

In one embodiment, the touch sensor controller 110 may output the digital touch sensing signal DTSS including the touch position coordinate information in response to the first enable signal EN1. The touch sensor controller 110 may output the moisture level MOIS in response to the second enable signal EN2. The touch sensor controller 110 may further output the digital touch sensing signal DTSS in response to the second enable signal EN2.

The amount of change in capacitance indicated by the touch sensor TS (that is, the sensing electrodes) may vary depending on the degree of moisture contained in skin contacting the display device 1000. For example, as the amount of skin moisture increases under substantially the same contact conditions, the electric field of a portion corresponding thereto is amplified. As a result, the capacitance of the sensing electrode (or the amount of change in capacitance) may increase. When skin becomes drier, wrinkles or other artifacts of the skin become deeper or more pronounced, and/or dead skin cells may occur. This may produce a commensurate decrease in capacitance.

The touch sensor controller 110 may digitize the change in the amount of moisture in skin based on the amount of change in capacitance. However, in some touch sensors which have been proposed, a change in capacitance corresponding to a change in the amount of moisture is made within a very small range, and the moisture level MOIS that may be expressed through this is inevitably limited. Therefore, an approximate or inaccurate numerical moisture level MOIS may be calculated based only on the change in capacitance of the touch sensor TS. This, in turn, may cause measurement accuracy to be poor. In addition, because environmental factors (for example, temperature, change in the characteristic of the contact surface of the display device 1000 in contact with the skin, etc.) other than skin moisture effect a change in capacitance, the accuracy (or reliability) of the moisture level MOIS calculated using the touch sensor TS may also be low.

To improve the accuracy and precision of a moisture level MOIS measurement, according to one or more embodiments the display device 1000 may correct the moisture level MOIS using data acquired through the fingerprint sensor FS.

In one embodiment, the fingerprint sensor controller 120 may include an analog-digital converter that converts a first sensing signal SS1 or a second sensing signal SS2 provided from the fingerprint sensor FS to a digital sensing signal DSS including fingerprint information and/or another body part information of a user.

In one embodiment, the fingerprint sensor controller 120 may control driving of the fingerprint sensor FS in the first mode in a manner different from driving the fingerprint sensor FS in the second mode. For example, the fingerprint sensor controller 120 may provide a first driving control signal FCON1 to the fingerprint sensor FS in response to the first enable signal EN1 activated in the first mode, and may provide a second driving control signal FCON2 to the fingerprint sensor FS in response to the second enable signal EN2 activated in the second mode The fingerprint sensor FS driven by the first driving control signal FCON1 may generate the first sensing signal SS1, and the fingerprint sensor FS driven by the second driving control signal FCON2 may generate the second sensing signal SS2. For example, when the fingerprint sensor FS includes photo-sensor pixels, a light exposure time of a photo sensor by the second driving control signal FCON2 may be longer than the light exposure time of the photo sensor by the first driving control signal FCON1. Accordingly, an image generated by the image processor 130 in the second mode may have a relatively high quality (or high image quality) compared with an image generated by the image processor 130 in the first mode.

For example, the fingerprint sensor controller 120 may control the driving and driving conditions of the fingerprint sensor FS so that image quality (for example, gray scale value, color balance, color reproduction, contrast, etc.) converted based on the second sensing signal SS2 in the second mode is higher than that based on the first sensing signal SS1 in the first mode.

The first sensing signal SS1 or the second sensing signal SS2 may be converted to the digital sensing signal DSS by the fingerprint sensor controller 120. The digital sensing signal DSS by the first sensing signal SS1 may include fingerprint information, and the digital sensing signal DSS by the second sensing signal SS2 may include information about a body (or body part) of a user who contacts the display device 1000 for measurement of the moisture level MOIS.

The image processor 130 may generate a fingerprint image FIM or a skin image SIM of a body from the digital sensing signal DSS. For example, the image processor 130 may image a digital sensing signal DSS using various known image processing techniques. Hereinafter, the fingerprint image FIM may be referred to as an image based on the first sensing signal SS1 generated in the first mode for fingerprint authentication, and the skin image SIM may be referred to as an image based on the second sensing signal SS2 generated based on a body part (for example, palm, finger, face, neck, arm, etc.) contacting the display device 1000 for measurement of a skin moisture level in the second mode. In other words, for better understanding and ease of description, the image calculated in the first mode may be referred to as the fingerprint image FIM, and the image calculated in the second mode may be referred to as the skin image SIM.

In some embodiments, the image processor 130 may perform additional image processing on the digital sensing signal DSS. For example, the image processor 130 may perform smoothing on imaged data based on the digital sensing signal DSS. Accordingly, contrast division between the fingerprint image FIM and the skin image SIM is improved, and noise and the like may be removed. The smoothing may be performed through histogram analysis for respective pixels in an original image, and in this case, for example, a median filter may be used. The smoothing may be performed by various types of processing algorithms.

The image processor 130 may generate the fingerprint image FIM and the skin image SIM by performing binarization and thinning on the image-processed digital sensing signal DDS. The image processor 130 may convert a plurality of gray scale levels (for example, at least one corresponding among 256 gray levels) to predetermined values, e.g., corresponding to 0 (black) or 1 (white). In this case, for example, the ridges of the fingerprint may be clearly distinguished by black, and the valleys configuring the fingerprint may be clearly distinguished by white. In addition, the image processor 130 may generate a line image having a ridge width of, for example, 1 pixel from the binarized image. Since the binarization and thinning are performed to improve the accuracy of fingerprint detection, they may be omitted when not needed.

In the embodiment, the image processor 130 may calculate skin characteristic data SCD from the digital sensing signal DSS and/or the skin image SIM. The skin characteristic data SCD may include skin wrinkle information and/or dead skin cell information. As skin becomes dry, the number of dead skin cells may increase and/or skin may contract and wrinkles may deepen. A change in skin condition may be estimated based on changes in wrinkles and dead skin cells through an analysis performed of the digital sensing signals DSS and/or the skin image SIM.

In one embodiment, a skin wrinkle may correspond to a bright value (or high gray scale value) similar to the valley of fingerprint. The depth of the wrinkle may be calculated, for example, based on a standard deviation of the brightness of the skin image SIM. For example, as the brightness of the image increases, it may be determined that the depth of the wrinkle is deeper. In addition, it may be determined that the deeper the wrinkle, the drier the skin.

In some embodiments, dead skin cell information may be extracted based on the difference between a most recently acquired skin image SIM and a currently acquired skin image SIM. For example, a change in skin condition may be additionally estimated based on the measured amount of change in the number or presence of dead skin cells of the skin. In addition, as the skin becomes dry, closely-contacting force between a surface of the display device 1000 and the skin may relatively decrease. Due to dehiscence between the skin and the surface of the display device 1000, white noise (e.g., in which the skin image SIM is brightened as a whole or a ratio of bright gray scale increases) may increase.

The image processor 130 may generate the skin characteristic data SCD of the skin image SIM, for example, by additionally analyzing a change amount or ratio of the white noise.

In the embodiment, the image processor 130 may include an artificial intelligence (AI) program or an AI module that generates and updates a detection (or machine-learning) model that calculates the skin characteristic data SCD including the degree of dryness of the skin from the digital sensing signal DSS and/or the skin image SIM. The image processor 130 may set a detection model for calculating the skin characteristic data SCD using deep learning-based AI technology. For example, the deep learning-based AI technology (or learning algorithm) may include a deep belief network, an autoencoder, a convolutional neural network (CNN), a recurrent neural network (RNN), a deep Q-network, or other machine-learning or AI model. These deep learning-based AI technologies are only examples any may correspond to different models in other embodiments.

In one embodiment, the skin characteristic data SCD including the wrinkle information and the dead skin cell information may be digitized and provided to the weight determiner 150 and the storage 140.

The fingerprint image FIM may be provided to the storage 140 and the fingerprint authenticator 160, and the skin image SIM and the skin characteristic data SCD may be provided to the weight determiner 150 and the storage 140.

In one embodiment, due to a difference in driving conditions of the fingerprint sensor in the first mode and the second mode and/or a difference in image filters used in the image processor 130, the image quality (or the quality) of the skin image SIM generated in the second mode may be higher than that of the fingerprint image FIM generated in the first mode. For example, to more accurately detect skin characteristics from the skin image SIM, image processing may be performed so that the image quality of the skin image SIM is higher than that of the fingerprint image FIM.

In addition, in one embodiment, the image processor 130 may differently apply image filters for improving a contrast ratio of the image to the skin image SIM and the fingerprint image FIM. For example, the contrast ratio of the skin image SIM for calculating the skin characteristic data SCD may be greater than that of the fingerprint image FIM.

The storage 140 may store the fingerprint image FIM, the skin image SIM, and the skin characteristic data SCD. For example, the storage 140 may be a non-volatile memory such as a erasable programmable read-only memory (EPROM), an electrically erasable programmable read-only memory (EEPROM), a flash memory, or a phase change random access memory (PRAM). The storage 140 may output stored fingerprint data S_FP to the fingerprint authenticator 160 based on the first enable signal EN1 in the first mode. The storage 140 may output a past skin image PSIM and/or a past skin characteristic data PSCD to the weight determiner 150 based on the second enable signal EN2 in the second mode.

The weight determiner 150 may calculate a weight by comparing the current skin characteristic data SCD and the past skin characteristic data PSCD. For example, the weight determiner 150 may calculate a weight applied to the moisture level MOIS by referring to the change in the skin characteristic data SCD accumulated in the second mode and may correct the moisture level MOIS. The weight may be added to or multiplied by the value of the moisture level MOIS. For example, the moisture level MOIS calculated by the touch sensor controller 110 for a predetermined skin condition may be expressed in predetermined increments, e.g., 10% units. In other embodiments, the moisture content C_MOIS) corrected by the weight calculated in the weight determiner 150 may be expressed up to about 1% (or 1% units) or about 0.1% (or 0.1% units).

In the embodiment, when it is determined that the skin condition is drier according to a result of comparing the skin characteristic data SCD and the past skin characteristic data PSCD (e.g., when SCD<PSCD), the weight determiner 150 may decrease a previously set weight or may set a negative weight. For example, the skin characteristic data SCD and the past skin characteristic data PSCD may be expressed as a numerical value of the degree of dryness of the skin. Accordingly, the corrected moisture level C_MOIS may have a value smaller than the moisture level MOIS. In addition, as the deviation between the skin characteristic data SCD and the past skin characteristic data PSCD increases, the amount of change in weight may increase.

In the embodiment, when the comparison result indicates that the skin condition is more moist (e.g., when SCD>PSCD), the weight determiner 150 may increase a previously set weight or may set a positive weight. Accordingly, the corrected moisture level C_MOIS may have a value greater than the moisture level MOIS.

When the skin condition indicated in the skin characteristic data SCD and the skin condition in the past skin characteristic data PSCD are determined to be substantially the same (e.g., or within a predetermined range), the weight determiner 150 may maintain the previously set weight or set the weight to 0. As such, the weight determiner 150 may correct the value of the moisture level MOIS to a more subdivided value by applying the weight to the moisture level MOIS.

In one embodiment, the past skin characteristic data PSCD output from the storage 140 may be data corresponding to the currently sensed moisture level MOIS. For example, when the currently sensed moisture level MOIS has a first value, the skin characteristic data SCD, stored when the moisture level MOIS was sensed as the first value in the past, is the weight that may be provided to the weight determiner 150 as the past skin characteristic data PSCD. In this case, the storage 140 may have a lookup table format, and the past skin characteristic data PSCD corresponding to the currently sensed moisture level MOIS may be read by the weight determiner 150. Accordingly, it may be possible to accurately estimate the moisture level in the skin condition corresponding to the moisture level MOIS.

However, the method of comparing the past skin characteristic data PSCD and the skin characteristic data SCD and determining the weight may be performed differently in another embodiment. For example, the weight determiner 150 may correct the weight through learning using accumulated skin characteristic data SCD and the comparison result. In the embodiment, the weight determiner 150 may include an AI program or AI module that generates and updates a model that calculates a weight through comparison of the skin characteristic data SCD and the past skin characteristic data PSCD. The weight determiner 150 may set a learning model that improves precision of a weight using deep learning-based AI technology.

The fingerprint authenticator 160 may perform fingerprint authentication by comparing the fingerprint image FIM and the stored fingerprint data S_FP. The fingerprint authenticator 160 may output a fingerprint authentication result as a matching signal MS.

As described above, according to one or more embodiments the display device 1000 may correct the moisture level MOIS of the skin, calculated through the capacitive touch sensor TS, based on the result (e.g., based on skin feature data SCD and past skin feature data PSCD) of analyzing the high-quality skin image SIM calculated through the fingerprint sensor FS. Accordingly, the accuracy and precision of the skin moisture measurement may be improved, and various numerical values of the skin moisture level may be expressed by the weight by the analysis of the skin image SIM.

FIGS. 4B and 4C illustrate embodiments of the operation of the sensor driver SDR of FIG. 4A. Referring to FIGS. 1A, 1B, 2, 4A, 4B, and 4C, the sensor driver SDR may perform the fingerprint authentication in the first mode and may measure the skin condition in the second mode. The fingerprint sensor controller 120 may provide the first driving control signal FCON1 to the fingerprint sensor FS in the first mode, and the fingerprint sensor controller 120 may provide the second driving control signal FCON2 to the fingerprint sensor FS in the second mode. Accordingly, operation of the fingerprint sensor FS may be activated in both the first mode and the second mode.

FIG. 4B shows an embodiment of the operation of the sensor driver SDR in response to the first enable signal EN1 in the first mode, and FIG. 4C shows an embodiment of the operation of the sensor driver SDR in response to the second enable signal EN2 in the second mode.

As shown in FIG. 4B, in the first mode, the touch sensor controller 110 may not calculate the moisture level MOIS. However, in the first mode, the touch sensor TS may sense a touch and may provide the touch sensing signal TSS to the touch sensor controller 110. In the first mode, the touch sensor controller 110 may convert the touch sensing signal TSS to the digital touch sensing signal DTSS including touch position coordinate information. Thus, in the first mode, the touch position may be sensed by the first touch sensor controller 110.

In addition, in the first mode, the image processor 130 may generate the fingerprint image FIM and may provide the fingerprint image FIM to the fingerprint authenticator 160. The fingerprint authenticator 160 may perform the fingerprint authentication by comparing the fingerprint image FIM and the stored fingerprint data S_FP. Thus, the fingerprint sensing and the fingerprint authentication may be performed in the first mode.

As shown in FIG. 4C, in the second mode, the touch sensor controller 110 may calculate the moisture level MOIS based on the touch sensing signal TSS. In addition, in the second mode, the image processor 130 may generate the skin image SIM and the skin characteristic data SCD. The weight determiner 150 may calculate a weight using the moisture level MOIS, the skin characteristic data SCD, and the past skin characteristic data PSCD and may generate the corrected moisture level C_MOIS.

In the second mode, the skin moisture level for a body part that a user wants to measure may be measured. For example, the skin moisture level of the body part (for example, palm, finger, face, neck, arm, etc.) contacting the display device 1000 may be measured. In the second mode, the fingerprint authenticator 160 may not operate.

Figure 5:
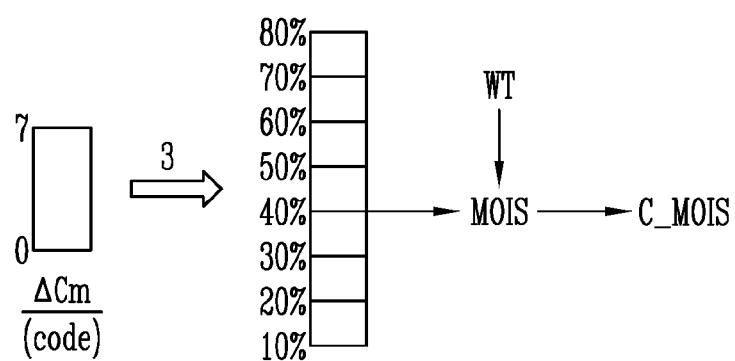
FIG. 5 illustrates an embodiment for generating a corrected moisture level.
Figure 6:
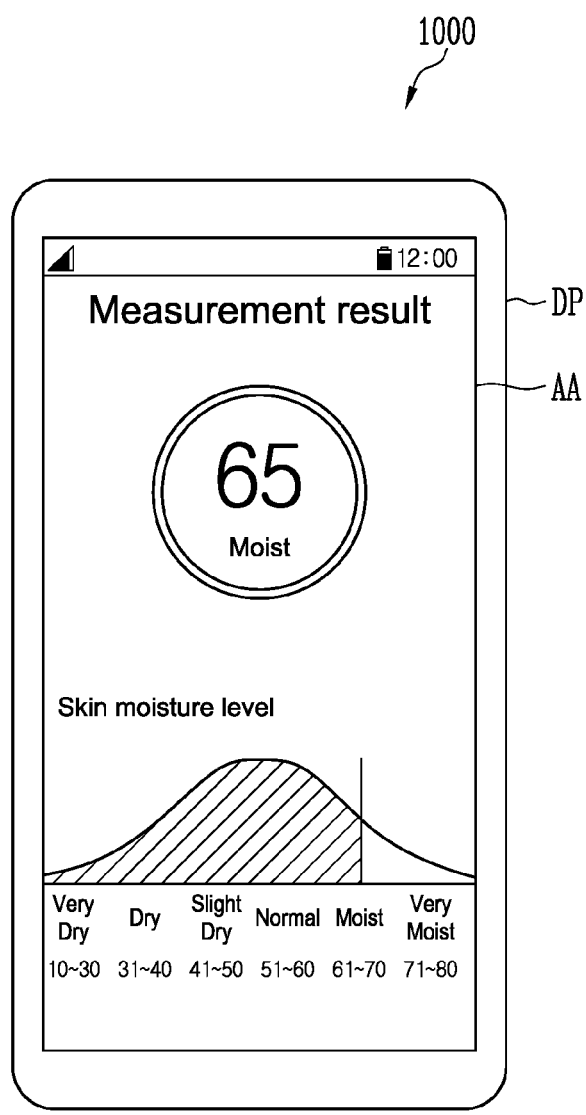
FIG. 6 illustrates an embodiment for displaying a moisture level.

FIG. 5 illustrates a diagram explaining an embodiment in which the sensor driver of FIG. 4A outputs a corrected moisture level, and FIG. 6 illustrates an embodiment of a moisture level displayed on a display panel by the sensor driver of FIG. 4A.

Referring to FIGS. 1, 4A, 5, and 6, the sensor driver SDR may calculate the corrected moisture level C_MOIS by applying a weight WT to the moisture level MOIS. As described above, the range of the significant change in capacitance that may distinguish the difference in the moisture content in a state in which the skin touches the touch sensor TS is very small. For example, the difference in the capacitance change amount $\Delta Cm$ is insignificant compared with the relatively large difference in the moisture content. As a result, the moisture level expression may be inaccurate. Also, the number of codes for converting the capacitance change amount $\Delta Cm$ to digital data may be limited. For example, as shown in FIG. 5, an ADC code based on the capacitance change amount $\Delta Cm$ may be divided into eight levels of 0 to 7. Accordingly, the moisture level MOIS may be expressed as one of eight values of 10% to 80%.

The touch sensor controller 110 may convert the capacitance change amount $\Delta Cm$ corresponding to the touch sensing signal TSS to the digital touch sensing signal DTSS. For example, in FIG. 5, the moisture level MOIS may indicate 40% by the digital touch sensing signal DTSS corresponding to the value of 3.

The weight WT determined by the image analysis of the image processor 130 and operation of the weight determiner 150 may be applied to the moisture level MOIS. For example, the corrected moisture level MOIS may indicate a value of about 43%, about 44.5%, or about 38%.

In the second mode, the display panel DP may display an image corresponding to the corrected moisture level C_MOIS in the display area AA. For example, the display driver DDR may be driven so that an image corresponding to the corrected moisture level C_MOIS may be displayed on the display area AA of the display panel DP.

Figure 7:
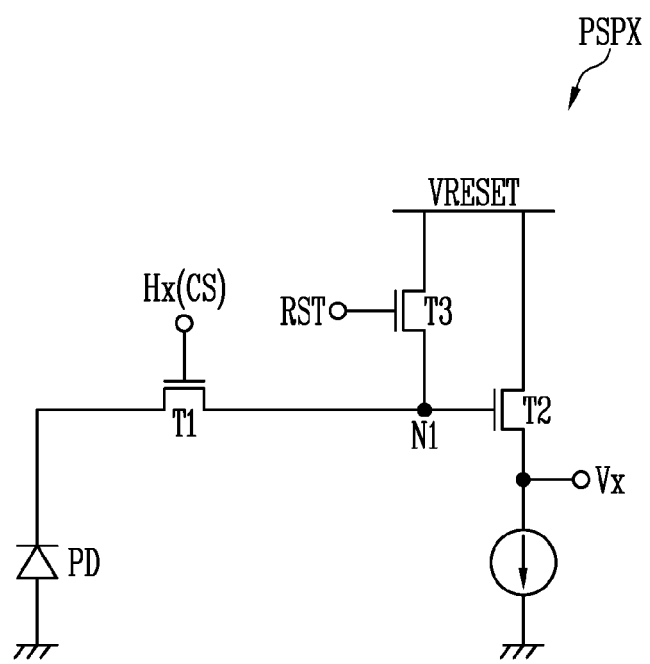
FIG. 7 illustrates an embodiment of a sensor pixel of a fingerprint sensor.

FIG. 7 illustrates an embodiment of a circuit diagram of a sensor pixel SPX of a fingerprint sensor of the display device of FIGS. 1A and 1B. Referring to FIGS. 1A, 1B, and 7, the sensor pixel SPX of the fingerprint sensor FS may include a photo sensor pixel PSPX. In the embodiment, the photo sensor pixel PSPX may include a photo diode (PD), a first transistor T1, a second transistor T2, and a third transistor T3. An example is shown in which the transistors are N-type transistors, but all or a portion of the transistors may be P-type transistors in another embodiment. In this case, the circuit structure of the photo sensor pixel SPX may be modified in a corresponding manner.

One electrode of the photo diode PD is grounded. The first transistor T1 may be connected between the photo diode PD and a first node N1. A gate electrode of the first transistor T1 may be connected to a driving line Hx. The first transistor T1 is turned on when a driving control signal CS is supplied to the driving line Hx, so that a charge photoelectrically converted by photo diode PD may be transmitted to the first node N1.

The third transistor T3 may be connected between a reset power source VRESET and the first node N1. A gate electrode of the third transistor T3 may receive a reset signal through a reset line RST. When the reset signal is applied, the third transistor T3 may be turned on to re-set a voltage of the first node N1 to a voltage of the reset power source VRESET.

The second transistor T2 may be connected between the reset power source VRESET and a signal line Vx. A gate electrode of the second transistor T2 is connected to the first node N1. The second transistor T2 may operate as an amplifier that outputs a signal corresponding to the voltage of the first node N1 to the signal line Vx. A signal output through the signal line Vx may be the sensing signal SS. The structure of the photo sensor pixel PSPX is not limited to the above and, for example, may include 4 or more or 2 or less transistors in other embodiments.

Figure 8:
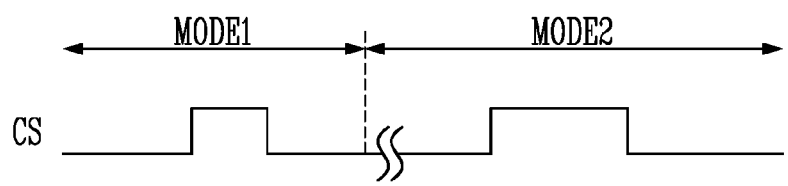
FIG. 8 illustrates an embodiment of a timing diagram for the sensor pixel.

FIG. 8 illustrates an embodiment of a timing diagram for driving the sensor pixel of FIG. 7. Referring to FIGS. 1A, 1B, 4A, 7, and 8, the fingerprint sensor controller 120 may supply the driving control signal CS to the photo sensor pixel PSPX. The fingerprint sensor controller 120 may differently control driving of the fingerprint sensor FS in the first mode and driving of the fingerprint sensor FS in the second mode.

In the embodiment, the pulse width of the driving control signal CS supplied in the second mode may be greater than that of the driving control signal CS supplied in the first mode. Accordingly, the turn-on time of the first transistor T1 in the second mode may be longer than that of the first transistor T1 in the first mode. For example, the fingerprint sensor controller 120 may allow the light exposure time of the photo sensor pixel PSPX in the second mode to be longer than that of the photo sensor pixel PSPX in the first mode. Accordingly, the image processor 130 may generate a skin image SIM of relatively high quality in the second mode. For example, the skin image SIM in the second mode may have higher quality than the fingerprint image FIM in the first mode. Therefore, reliability of the skin characteristic data SCD may be improved.

Figure 9:
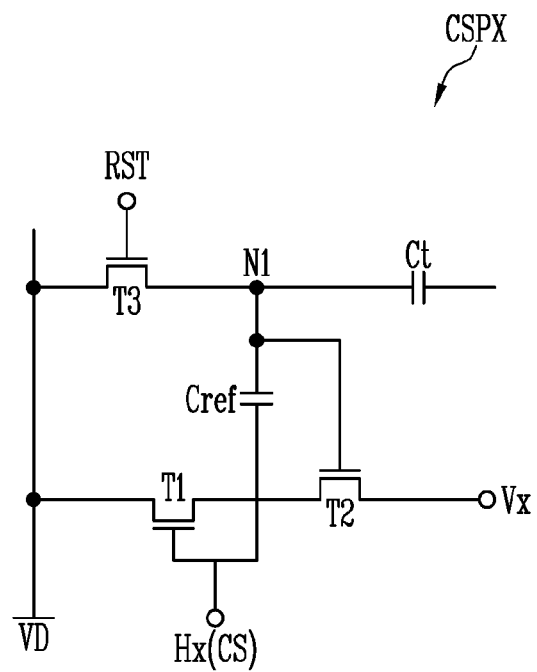
FIG. 9 illustrates an embodiment of a sensor pixel of a fingerprint sensor.

FIG. 9 illustrates an embodiment of a circuit diagram of a sensor pixel of a fingerprint sensor of the display device of FIGS. 1A and 1B. In FIG. 9, the same reference numerals for like constituent elements described with reference to FIG. 7 are used.

Referring to FIGS. 1A, 1B, and 9, the sensor pixel SPX of the fingerprint sensor FS may include a capacitive sensor pixel CSPX. In the embodiment, the capacitance sensor pixel CSPX may include a touch capacitor Ct, a reference capacitor Cref, a first transistor T1, a second transistor T2, and a third transistor T3. In the capacitance sensor pixel CSPX, a change in capacitance may occur in the touch capacitor Ct according to the touch of the skin. The first to third transistors T1 to T3 may perform a function substantially equivalent to that performed by the first to third transistors T1 to T3 described with reference to FIG. 7.

One electrode of the touch capacitor Ct is connected to the first node N1, and the touch capacitor Ct may be electrically connected by a user touch. The reference capacitor Cref may be connected between the first node N1 and the driving line Hx.

The first transistor T1 may be connected between a driving power source VD and the second transistor T2. A gate electrode of the first transistor T1 may be connected to the driving line Hx. The first transistor T1 may be turned on when the driving control signal CS is supplied to the driving line Hx to transmit a voltage of the driving power source VD to the second transistor T2. In this case, a signal (voltage) based on a capacitance ratio between the touch capacitor Ct and the reference capacitor Cref may be supplied to the first node N1.

The third transistor T3 may be connected between the driving power source VD and the first node N1. A gate electrode of the third transistor T3 may receive the reset signal through the reset line RST. When the reset signal is applied, the third transistor T3 may be turned on to re-set a voltage of the first node N1 to a voltage of the driving power source VD.

The second transistor T2 may be connected between the first transistor T1 and the signal line Vx. A gate electrode of the second transistor T2 is connected to the first node N1. The second transistor T2 may operate as an amplifier that outputs a signal corresponding to the voltage of the first node N1 to the signal line Vx. A signal output through the signal line Vx may be the sensing signal SS. The structure of the capacitance sensor pixel CSPX is not limited to the above and, for example, may include 4 or more or 2 or less transistors in other embodiments.

The fingerprint sensor controller 120 may supply the driving power VD and the driving control signal CS to the capacitance sensor pixel CSPX. In one embodiment, the fingerprint sensor controller 120 may provide at least one of a voltage level of the driving power source VD, a frequency of the driving control signal CS, or a pulse width of the driving control signal CS differently from each other in the first mode and the second mode. The fingerprint sensor controller 120 may control the driving power source VD and/or the driving control signal CS so that the skin image SIM in the second mode may have higher image quality than the fingerprint image FIM in the first mode.

Figure 10:
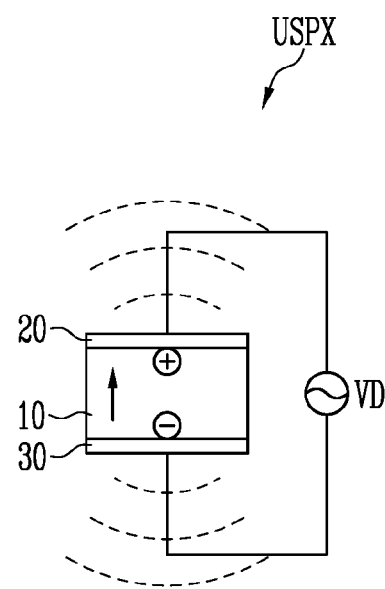
FIG. 10 illustrates an embodiment of a sensor pixel of a fingerprint sensor.

FIG. 10 illustrates an embodiment of a circuit diagram of a sensor pixel of a fingerprint sensor of the display device of FIGS. 1A and 1B. Referring to FIGS. 1A, 1B, and 10, the sensor pixel SPX of the fingerprint sensor FS may include an ultrasonic sensor pixel USPX. The ultrasonic sensor pixel USPX may operate as an ultrasonic transmitter or ultrasonic receiver. In the embodiment, the ultrasonic sensor pixel USPX may include a first electrode 20, a second electrode 30, and a piezoelectric layer 10 between the first electrode 20 and the second electrode 30.

In the embodiment, the fingerprint sensor controller 120 may supply the driving power source VD for ultrasonic oscillation to the ultrasonic sensor pixel USPX. The driving power source VD may be an AC power source. Frequencies of the driving power source VD in the first mode and the second mode may be different from each other. For example, the fingerprint sensor controller 120 may differently control the frequencies of the driving power source VD according to respective modes so that the skin image SIM in the second mode may have higher quality than fingerprint image FIM in the first mode.

Figure 11A:
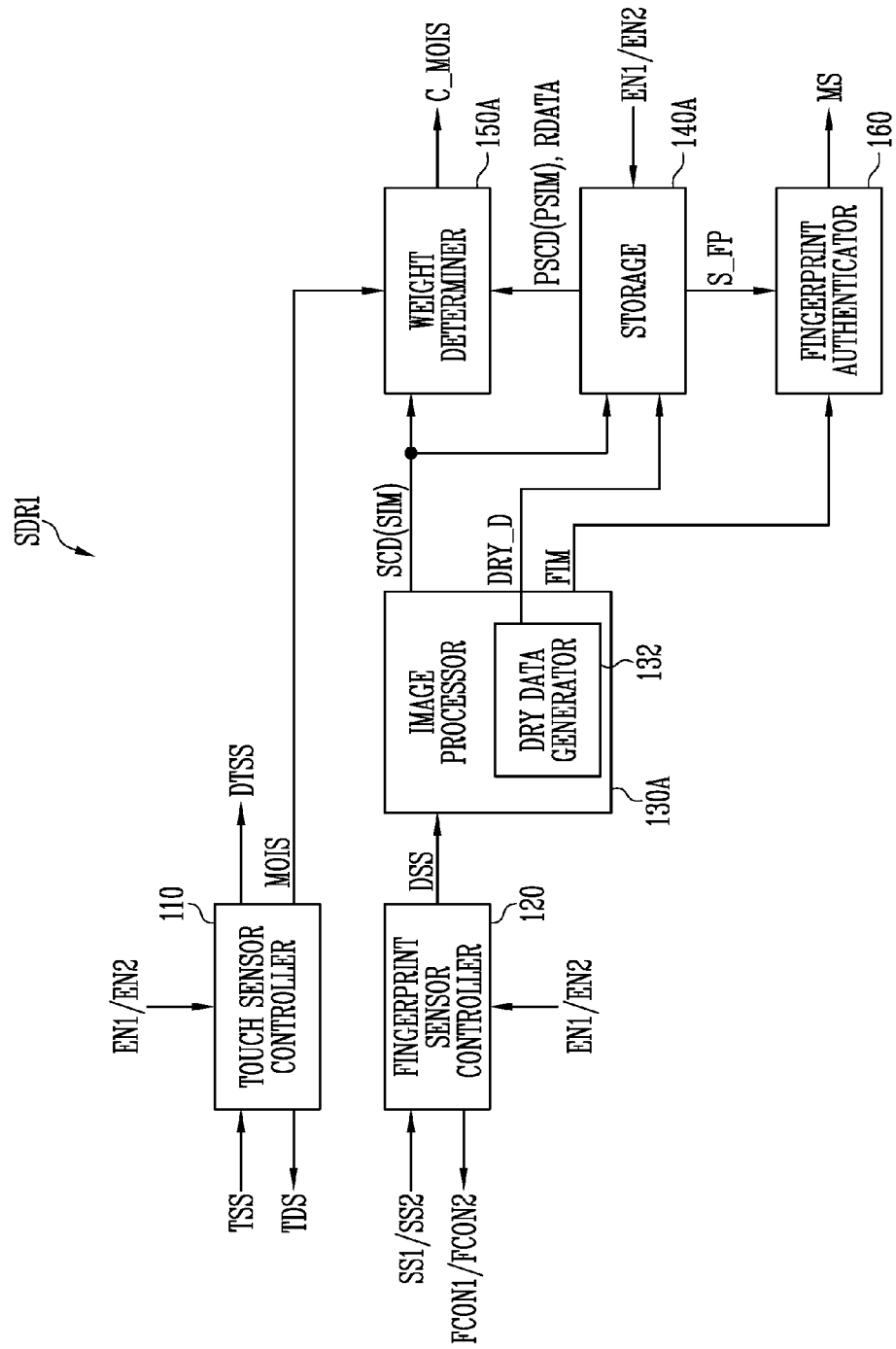
FIG. 11A illustrates an embodiment of a sensor driver.

FIG. 11A illustrates an embodiment of a sensor driver in or coupled to the display device of FIGS. 1A and 1B. In FIG. 11A, the same reference numeral may be used for like constituent elements described with reference to FIG. 4A.

Referring to FIGS. 1A, 1B, 2, and 11A, a sensor driver SDR1 includes the touch sensor controller 110, the fingerprint sensor controller 120, an image processor 130A, a storage 140A, a weight determiner (or calculator) 150A, and the fingerprint authenticator 160.

As described above, the fingerprint image FIM may be referred to as an image based on the first sensing signal SS1 generated in the first mode for fingerprint authentication. The skin image SIM may be referred to as an image based on the second sensing signal SS2 generated based on a body part (for example, palm, finger, face, neck, arm, etc.) contacting the display device 1000 for measurement of the skin moisture level in the second mode. In other words, the image calculated in the first mode may be referred to as the fingerprint image FIM and the image calculated in the second mode may be referred to as the skin image SIM.

The image processor 130A may generate the fingerprint image FIM or the skin image SIM of the body from the digital sensing signal DSS. In one embodiment, the image processor 130A may include a dry data generator 132. The dry data generator 132 may generate dry data DRY_D by analyzing a ratio of white noise in the fingerprint image FIM in the first mode and comparing the ratio of white noise with a predetermined threshold value. For example, when the ratio of white noise exceeds the threshold value, it may be determined that the skin at the time of authentication of a corresponding fingerprint is dry and thus dry data DRY_D may be generated. The generated dry data DRY_D may be stored in the storage 140A.

When the ratio of white noise is less than or equal to the threshold value, it is determined that the skin at the time of authentication of the fingerprint is not dry and thus the dry data DRY_D is not generated.

The weight determiner 150A may calculate a weight by comparing the current skin characteristic data SCD and the past skin characteristic data PSCD. In addition, the weight determiner 150A may additionally correct the weight based on a ratio (or frequency) of the dry data DRY_D to the number of fingerprint inputs (or the number of activations of the first mode). The number of fingerprint inputs and the dry data DRY_D may be provided from the storage 140A as additional reference data RDATA.

The number of fingerprint inputs may correspond to the number of times the first mode is activated (or the number of times the fingerprint image is generated) from after the immediately previous second mode is deactivated until the current second mode is activated. For example, when the number of fingerprint inputs is 100 times and the dry data DRY_D is generated 70 times for the 100 fingerprint inputs, a ratio of the dry data DRY_D to the number of fingerprint inputs (hereinafter referred to as a dry fingerprint ratio) may be less than or equal to about 70%.

The weight determiner 150A may further reflect the dry fingerprint ratio to the weight. In the embodiment, when the dry fingerprint ratio exceeds a predetermined threshold range, the skin may be determined to be relatively dry and the weight determiner 150A may further correct the corrected moisture level C_MOIS to have a lower value.

When the dry fingerprint ratio is less than predetermined threshold range, the skin may be determined to be relatively moist and the weight determiner 150A may further correct the corrected moisture level C_MOIS to have a higher value.

When the dry fingerprint ratio is within the threshold range, the weight determiner 150A may not perform additional correction for the corrected moisture level C_MOIS.

The method of additionally correcting the weight using the above-described dry data DRY_D is an example. The driving method of correcting the moisture level C_MOIS to a more precise value may be different in another embodiment.

As such, the sensor driver SDR1 as shown in FIG. 11A may additionally analyze the dryness degree of the fingerprint image sensed in the first mode and may additionally reflect the dry fingerprint input ratio at the time of fingerprint authentication to the weight used to calculate the skin moisture level in the subsequent second mode.

Figure 11C:
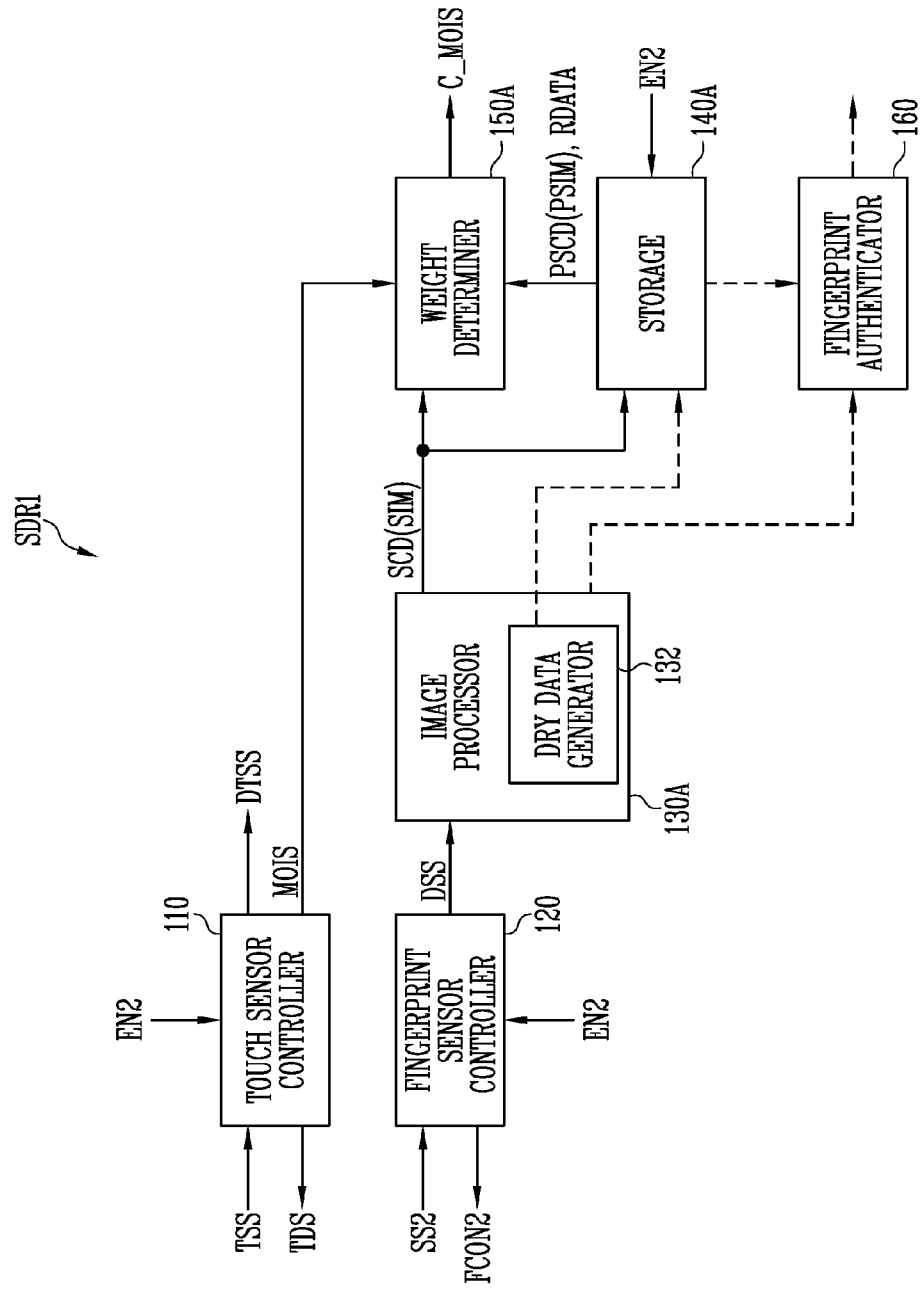

FIGS. 11B and 11C illustrate embodiments of the operation of the sensor driver SDR1 of FIG. 11A. Referring to FIGS. 1A, 1B, 2, and 11A to 11C, the sensor driver SDR1 may perform fingerprint authentication in the first mode and may measure skin condition in the second mode. Operation of the fingerprint sensor FS may be activated in both the first mode and the second mode. FIG. 11B shows an example of the operation of sensor driver SDR1 in response to the first enable signal EN1 in the first mode, and FIG. 11C shows an example of the operation of sensor driver SDR1 in response to the second enable signal EN2 in the second mode.

As shown in FIG. 11B, in the first mode, the dry data generator 132 of the image processor 130A may generate dry data DRY_D using the fingerprint image FIM. The number of fingerprint inputs and the dry data DRY_D may be accumulated in the storage 140A.

As shown in FIG. 11C, in the second mode, the weight determiner 150A may generate the corrected moisture level C_MOIS using the moisture level MOIS, the skin characteristic data SCD, the past skin characteristic data PSCD, and the dry fingerprint ratio (e.g., calculated from the reference data RDATA). For example, the dry fingerprint ratio may be additionally reflected in the operation performed in the second mode (described with reference to FIGS. 4A and 4C) to generate the corrected moisture level C_MOIS.

Figure 12A:
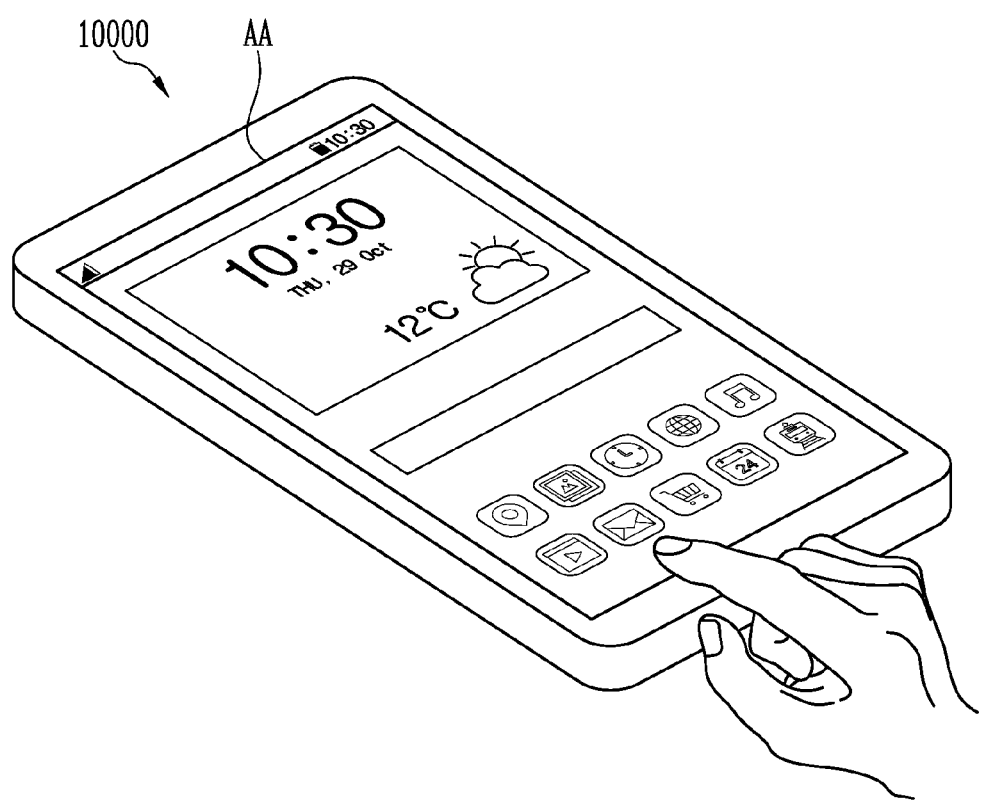
FIGS. 12A and 12B illustrate embodiments of an electronic device.
Figure 12B:
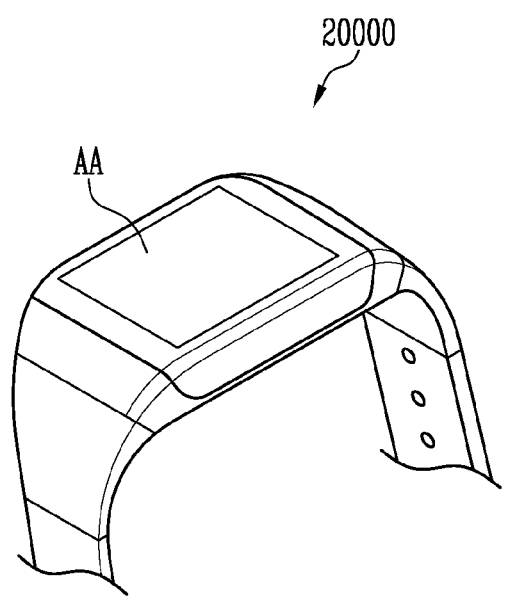

FIGS. 12A and 12B illustrate embodiments of an electronic device 1000 to which a display device according to the embodiments described herein may be applied.

Referring to FIGS. 1 to 12B, the display device 1000 may be applied to various types of electronic devices 10000 and 20000. In the embodiment of FIG. 12A, the display device 1000 (which performs skin measurement using touch sensor TS and fingerprint sensor FS) may be applied to a mobile device such as a smartphone. The skin measurement data as shown in FIG. 6 may be displayed as an image through the display area AA. In the embodiment of FIG. 12B, the display device 1000 (which performs the skin measurement using touch sensor TS and fingerprint sensor FS) may be applied to a wearable device such as a smart watch. The skin measurement data as shown in FIG. 6 may be displayed as an image through the display area AA.

Figure 13:
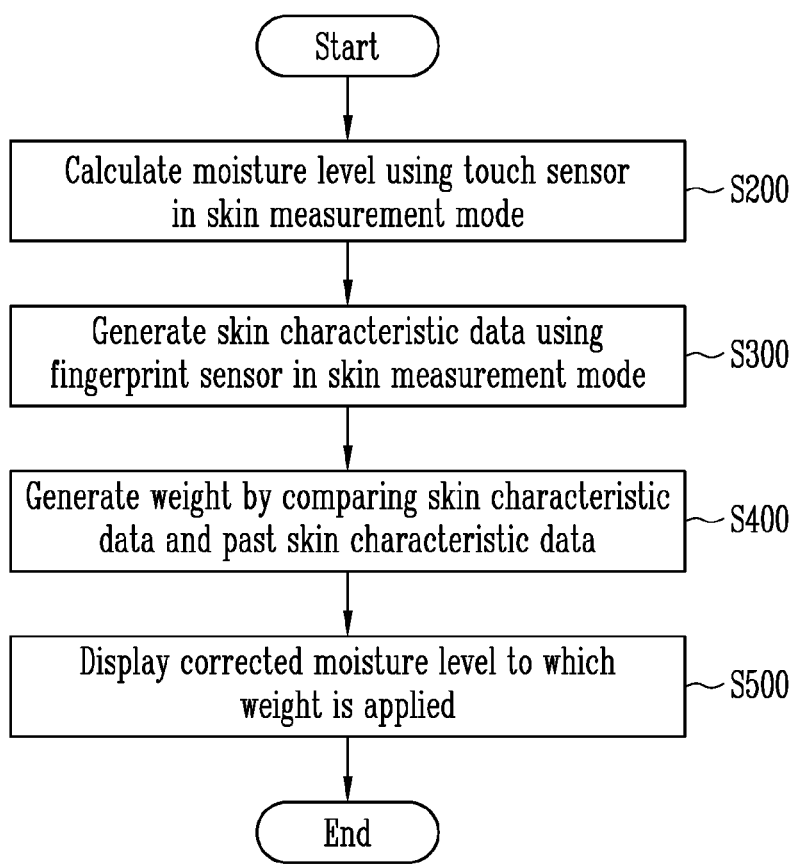
FIG. 13 illustrates an embodiment of a method of driving a display device.

FIG. 13 illustrates a flowchart of an example of a method of driving a display device according to an embodiment of the present invention. Referring to FIG. 13, the method may include calculating moisture level using a touch sensor in skin measurement mode (S200), generating skin characteristic data using a fingerprint sensor in the skin measurement mode (S300), generating a weight by comparing the skin measurement data and past skin characteristic data (S400), and displaying an image corresponding to the corrected moisture level by applying the weight to the moisture level (S500).

In the skin measurement mode, the moisture level may be calculated using the touch sensing signal generated by the touch sensor (S200). For example, the skin moisture level of a user may be calculated based on a change in capacitance of the touch sensing signal output from the capacitive touch sensor.

In the skin measurement mode, the skin characteristic data may be generated using the skin sensing signal (for example, digital sensing signal) generated by the fingerprint sensor (S300). The fingerprint sensor is activated even in the skin measurement mode, and a skin image (e.g., skin image data) may be generated through image processing of the skin sensing signal. Here, information such as dead skin cells and wrinkles may be determined through analysis of the skin image.

In the skin measurement mode, a weight may be generated by comparing the skin measurement data and accumulated past skin characteristic data (S400). For example, a relative change in skin condition may be determined based on a comparison of the skin measurement data and past skin characteristic data. This change in skin condition may be expressed as a weight or other numerical value. The moisture level corrected by the weight may be displayed as an image (S500). Operations of this method may correspond to those previously described, for example, with respect to FIGS. 1A to 10.

FIG. 14 illustrates a flowchart of another embodiment of a method of driving a display device. The embodiment of FIG. 14 may be substantially the same as the driving method of the display device of FIG. 13, except for a method of calculating dry data in the fingerprint authentication mode and for correcting a weight using the dry data in the skin measurement mode. Accordingly, in FIG. 14, the same reference numeral for the constituent elements described with reference to FIG. 13 is used, and redundant descriptions of these constituent elements will be omitted.

Referring to FIG. 14, the method includes generating a fingerprint image using the fingerprint sensing signal generated by the fingerprint sensor in the fingerprint authentication mode (S100), generating and storing dry data by analyzing the ratio of white noise in the fingerprint image in the fingerprint authentication mode (S150), and additionally correcting a weight based on a ratio of the stored dry data to the number of fingerprint authentication in the fingerprint authentication mode, in the skin measurement mode (S450). Thus, the driving method of FIG. 14 may additionally analyze the degree of dryness of fingerprint images generated in the fingerprint authentication mode, and may additionally reflect an input ratio of the dry fingerprint to the weight during the fingerprint authentication. Accordingly, the frequency of measuring the change in skin condition may increase and the accuracy of measuring moisture level may be improved.

In one embodiment, driving of the fingerprint sensor in the fingerprint authentication mode and driving of the fingerprint sensor in the skin measurement mode may be differently controlled. For example, driving of the fingerprint sensor may be controlled so that the quality of the skin image (skin image data) detected in the skin measurement mode may be higher than the quality of the fingerprint image (fingerprint image data) detected in the fingerprint authentication mode.

In one embodiment, a non-transitory computer-readable medium stores instructions which, when executed by one or more processors, performs operations of the embodiments described herein. The computer-readable medium may be any type of volatile or non-volatile memory, and the one or more processors may correspond to any combination of the drivers, controllers, or processors of the aforementioned embodiments. For example, when the instructions are executed by the one or more processors, the one or more processors may calculate moisture level using a touch sensing signal generated by a touch sensor in a skin measurement mode, generate skin characteristic data using a skin sensing signal generated by a fingerprint sensor in the skin measurement mode, generate a weight based on a comparison of the skin characteristic data with accumulated past skin characteristic data, correct the moisture level based on the weight, and display an image indicating the corrected moisture level.

In one embodiment, a display device includes a fingerprint sensor and a sensor driver. The fingerprint sensor is disposed to be spaced apart from a touch sensor and is configured to detect an object in a first mode to generate a first sensing signal and to detect the object in a second mode to generate a second sensing signal. The sensor driver calculates a touch position and a moisture level of the object based on the touch sensing signal, generates fingerprint information based on the first sensing signal, and corrects the moisture level based on the second sensing signal.

In accordance with one or more of the aforementioned embodiments, a method of driving a display device is provided which may correct the moisture level of the skin calculated through a capacitive touch sensor. This may be performed based on an analysis of a high-quality skin image calculated through the fingerprint sensor. Accordingly, the accuracy and precision of skin moisture measurement may be improved, and various numerical values of skin moisture level may be expressed by the weight by the skin image analysis.

While this invention has been described in connection with what is presently considered to be practical embodiments, it is to be understood that the invention is not limited to the disclosed embodiments, but, on the contrary, is intended to cover various modifications and equivalent arrangements included within the spirit and scope of the appended claims. The embodiments may be combined to form additional embodiments.

What is claimed is:

1. A display device, comprising:
   a display panel including pixels;
   a touch sensor disposed on a surface of the display panel and configured to generate a touch sensing signal in response to touch of an object;
   a fingerprint sensor disposed to be spaced apart from the touch sensor, configured to detect a fingerprint of the object at a first light exposure time in a first mode to generate a first sensing signal, and configured to detect skin characteristics of the object at a second light exposure time in a second mode to generate a second sensing signal, the second light exposure time different from the first light exposure time;
   a sensor driver configured to calculate a touch position and a moisture level of the object based on the touch sensing signal, generate fingerprint information based on the first sensing signal, and correct the moisture level based on the second sensing signal, wherein a skin image based on the second sensing signal is of higher quality than a fingerprint image based on the first sensing signal,
   wherein the sensor driver comprises a calculator configured to calculate a weight by comparing skin characteristic data of the skin image with past skin characteristic data of a past skin image stored in the storage,
   wherein, when the skin characteristic data is smaller than the past skin characteristic data, the calculator is configured to calculate a negative weight and correct the moisture level to be decreased based on the negative weight, and
   wherein, when the skin characteristic data is greater than the past skin characteristic data, the calculator is configured to calculate a positive weight and correct the moisture level to be increased based on the positive weight.

2. The display device of claim 1, wherein the sensor driver comprises:
   a fingerprint sensor controller configured to differently control driving of the fingerprint sensor in the first mode and driving of the fingerprint sensor in the second mode; and
   a touch sensor controller configured to control driving of the touch sensor and calculate the moisture level based on the touch sensing signal.

3. The display device of claim 2, wherein the sensor driver further comprises:
   an image processor configured to generate the fingerprint image based on the fingerprint information, generate the skin image based on the second sensing signal, and extract skin characteristic data from the skin image; and
a storage configured to store the skin characteristic data.

4. The display device of claim 3, wherein an image quality of the skin image generated in the second mode is higher than an image quality of the fingerprint image generated in the first mode.

5. The display device of claim 4, wherein:
the image processor is configured to differently apply image filters that increase contrast ratio to the skin image and the fingerprint image, and
a contrast ratio of the skin image is greater than a contrast ratio of the fingerprint image.

6. The display device of claim 3, wherein the fingerprint sensor includes a photo sensor pixel including a photo diode.

7. The display device of claim 6, wherein:
the fingerprint sensor controller is configured to supply a driving control signal to the photo sensor pixel, and
a pulse width of the driving control signal supplied in the second mode is greater than a pulse width of the driving control signal supplied to the first mode.

8. The display device of claim 6, wherein the fingerprint sensor controller is configured to control a light exposure time of the photo sensor pixel in the second mode to be longer than a light exposure time of the photo sensor pixel in the first mode.

9. The display device of claim 3, wherein:
the fingerprint sensor includes a capacitive sensor pixel,
the fingerprint sensor controller is configured to supply a driving power source and a driving control signal to the capacitive sensor pixel, and
at least one of a voltage level of the driving power source or a frequency of the driving control signal in the first mode and the second mode is different from each other.

10. The display device of claim 3, wherein:
the fingerprint sensor includes an ultrasonic sensor pixel,
the fingerprint sensor controller is configured to supply a driving power source for ultrasonic oscillation to the ultrasonic sensor pixel, and
frequencies of the driving power source in the first mode and the second mode are different from each other.

11. The display device of claim 3, wherein:
the sensor driver is configured to perform fingerprint authentication based on the fingerprint information in the first mode and to calculate and correct the moisture level for a skin contacted in the second mode, and
the display panel is configured to display the corrected moisture level in the second mode.

12. The display device of claim 3, wherein the image processor comprises:
a dry data generator configured to analyze a ratio of white noise in the fingerprint image in the first mode and to generate dry data from the fingerprint image by comparing the ratio of the white noise with a predetermined threshold value.

13. The display device of claim 12, wherein:
the storage is configured to store the dry data, and
in the second mode, the calculator is configured to correct the weight based on a ratio of the dry data to a number of fingerprint inputs.

14. The display device of claim 3, wherein the current skin characteristic data is generated by an artificial intelligence model.

15. The display device of claim 1, wherein the image processor is configured to calculate the wrinkle and dead skin cell information as skin characteristic data based on gray scale levels of the skin image.

16. The display device of claim 1, wherein the calculator is configured to correct the weight through machine learning using accumulated skin characteristic data and the comparison result.

17. The display device of claim 1, wherein the calculator is configured to correct a value of the moisture level by applying the weight to the moisture level.

18. The display device of claim 1, wherein:
the first exposure time produces the fingerprint image;
the second exposure time produces the skin image; and
the skin image is used exclusively by the sensor driver to detect the skin characteristics.

19. The display device of claim 1, wherein, when the skin characteristic data is the same as the past skin characteristic data, the calculator is configured to correct the moisture level to a more subdivided value by applying the weight to the moisture level.

20. A method of driving a display device, comprising:
calculating a moisture level using a touch sensing signal generated by a touch sensor in a skin measurement mode;
generating skin characteristic data using a skin sensing signal generated by a fingerprint sensor in the skin measurement mode different from a fingerprint authentication mode;
generating a weight based on a comparison of the skin characteristic data with accumulated past skin characteristic data;
correcting the moisture level based on the weight; and
displaying an image indicating the corrected moisture level,
wherein a skin image based on the skin sensing signal is of higher quality than a fingerprint image based on the touch sensing signal,
wherein, when the skin characteristic data is smaller than the past skin characteristic data, the corrected moisture level has a value smaller than the moisture level, and
wherein, when the skin characteristic data is greater than the past skin characteristic data, the corrected moisture level has a value greater than the moisture level.

21. The method of claim 20, further comprising:
generating a fingerprint image using a fingerprint sensing signal generated by the fingerprint sensor in the fingerprint authentication mode;
generating and storing dry data by analyzing a ratio of white noise in the fingerprint image; and
in the skin measurement mode, correcting the weight based on a ratio of the stored dry data to a number of fingerprint authentication in the fingerprint authentication mode.

22. The method of claim 21, wherein the fingerprint sensor is driven in the fingerprint authentication mode in a manner different from driving the fingerprint sensor in the skin measurement mode.

23. A non-transitory computer-readable medium storing instructions which, when executed by one or more processors, cause the one or more processors to:
calculate a moisture level using a touch sensing signal generated by a touch sensor in a skin measurement mode;
generate skin characteristic data using a skin sensing signal generated by a fingerprint sensor in the skin measurement mode different from a fingerprint authentication mode;
generate a weight based on a comparison of the skin characteristic data with accumulated past skin characteristic data;

correct the moisture level based on the weight; and
display an image indicating the corrected moisture level,
wherein a skin image based on the skin sensing signal is
of higher quality than a fingerprint image based on the
touch sensing signal,
wherein, when the skin characteristic data is smaller than
the past skin characteristic data, the corrected moisture
level has a value smaller than the moisture level, and
wherein, when the skin characteristic data is greater than
the past skin characteristic data, the corrected moisture
level has a value greater than the moisture level.

\* \* \* \* \*